(12) United States Patent
Boyle

(10) Patent No.: US 6,414,174 B1
(45) Date of Patent: Jul. 2, 2002

(54) TIN(II) ALKOXIDE HYDROLYSIS PRODUCTS FOR USE AS BASE CATALYSTS

(75) Inventor: Timothy J. Boyle, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 31 days.

(21) Appl. No.: 09/815,870

(22) Filed: Mar. 22, 2001

(51) Int. Cl.[7] .............................. C07F 7/22; B01J 31/00
(52) U.S. Cl. .................................... 556/83; 502/150
(58) Field of Search ...................... 556/83; 502/150

(56) References Cited

U.S. PATENT DOCUMENTS

| 4,496,776 A | * | 1/1985 | Edwards et al. | ............ 568/827 |
|---|---|---|---|---|
| 4,549,017 A | * | 10/1985 | McEntire et al. | ............ 544/168 |
| 4,613,673 A | * | 9/1986 | McEntire et al. | ............ 502/155 |
| 4,675,411 A | * | 6/1987 | Sommer et al. | ............ 546/292 |
| 4,686,315 A | * | 8/1987 | Beach et al. | ................ 502/117 |

\* cited by examiner

Primary Examiner—Porfirio Nazario-Gonzalez
(74) Attorney, Agent, or Firm—Elmer A. Klavetter

(57) ABSTRACT

Tin alkoxide compounds are provided with accessible electrons. The compounds are a polymeric tin alkoxide, $[Sn(OCH_2C(CH_3)_3)_2]_n$, and the hydrolysis products $Sn_6O_4(OCH_2C(CH_3)_3)_4$ and $Sn_5O_2(OCH_2C(CH_3)_3)_6$. The hydrolysis products are formed by hydrolyzing the $[Sn(OCH_2C(CH_3)_3)_2]_n$ in a solvent with controlled amounts of water, between 0.1 and 2 moles of water per mole of the polymeric tin alkoxide.

20 Claims, 3 Drawing Sheets

(a)

(b)

TIN(II) ALKOXIDE HYDROLYSIS PRODUCTS FOR USE AS BASE CATALYSTS

This invention was made with Government support under Contract No. DE-AC04-94AL85000 awarded by the Department of Energy. The Government has certain rights in the invention.

BACKGROUND OF THE INVENTION

The present invention relates generally to metal alkoxide compounds and more particularly to a tin alkoxide and its hydrolysis derivatives and their method of preparation.

Tin alkoxides are used in applications ranging from electro-active ceramics, conductors, semiconductors, and catalysts. Even though the shape and type of metal cation structures used for metal alkoxide architecture can be well controlled at the atomic-level, metal alkoxides have not been generally used as catalysts. Typically those metal alkoxides that are used as catalysts involve alkali metal alkoxides. Alkyl aluminum alkoxides have also been used as part of a complex mixture to oligomerize ethylene (U.S. Pat. No. 4,686,315, issued on Aug. 11, 1987). There are also some reports of Group IV metal alkoxide for the production of polyacrylates, polyamides, and allylic alcohols (U.S. Pat. No. 4,496,776, issued on Jan. 29, 1985; U.S. Pat. No. 4,549,017, issued on Oct. 22, 1985). However, in general these materials are used as supports and not necessarily the active site of polymerization.

Sommer et al. (U.S. Pat. No. 4,675,411, issued on Jun. 23, 1987) and McEntire et al. (U.S. Pat. No. 4,613,673, issued on Sep. 23, 1986) using tin alkoxides have been reported; however, these compounds are reacted to form in situ compounds that are not metal alkoxides but metal amides. Sita et al. (Sita L., Xi, R., Yap, G., Liable-Sands, L., and Rheingold, A., "High Yield Synthesis and Characterization of $Sn_6(\mu_3\text{-}O)_4(\mu_3\text{-}OSi(CH_3)_3)_4$" 1997, J. Am. Chem. Soc., 119, 756–760) describes the synthesis and characterization of a tin-based compound with an inorganic cluster, $Sn_6(\mu_3\text{-}O)_4(\mu_3\text{-}OSi(CH_3)_3)_4$.

The low use of metal alkoxides as catalysts is typically attributed to the large charge/cation size ratio that leads to cluster formation to satisfy the various cation's coordination sphere demands. Because of this hyper-oligomerization, reactive sites on the metal are rendered inaccessible. Even for those metal alkoxides that do not oligomerize, ligand rearrangement results in solution functionality that again can neutralize potential active sites. Thus, metal alkoxides are typically poor catalysts due to hindered reactive sites. This is typically due to the dynamic behavior metal alkoxide compounds exhibit in solution coupled with the large cation to small charge ratio that promotes oligomerization.

DETAILED DESCRIPTION OF THE INVENTION

The present invention relates to tin alkoxide compositions that have availability of electrons in the structure of the tin alkoxides. These compounds, polymeric $Sn(OCH_2C(CH_3)_3)_2$ and its hydrolysis products, $Sn_6O_4(OCH_2C(CH_3)_3)_4$ and $Sn_5O_2(OCH_2C(CH_3)_3)_6$, have been formulated maintaining tin as Sn(II) rather than Sn(IV) to provide a structure that has accessible electrons (the Sn lone pair of electrons) and that, unlike other metal alkoxides, does not have dynamic behavior in solution that can neutralize effective active sites. These accessible electrons enable the compounds to be used as base catalysts or as bases in other reactions. The compounds can advantageously be used in solution or as thin films. The compounds can also be used as reagents in metal-organic chemical vapor deposition reactions.

Figure 1:
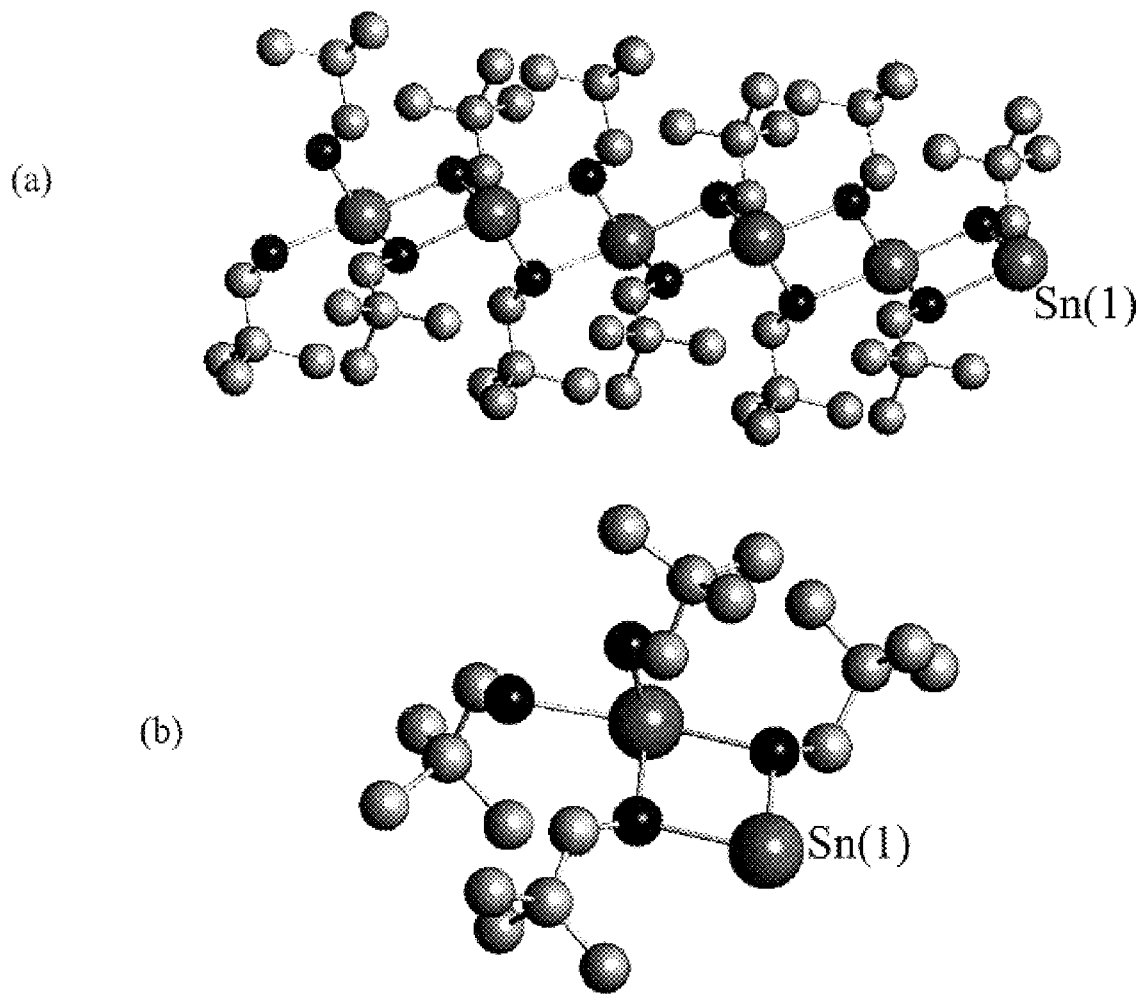
FIG. 1 illustrates the structure of $[Sn(OCH_2C(CH_3)_3)_2]_n$ in a ball and stick diagram: (a) polymer and (b) fragment.

According to the present invention, one compound formulated with accessible electrons is a polymeric tin alkoxide, referred hereinafter as polymeric $Sn(OCH_2C(CH_3)_3)_2$, or $[Sn(OCH_2C(CH_3)_3)_2]_n$, the structure of which is illustrated in FIG. 1. By controlled hydrolysis, certain hydrolysis products can be formulated which also have accessible electrons. These hydrolysis products include $Sn_6O_4(OCH_2C(CH_3)_3)_4$, illustrated in FIG. 2, and $Sn_5O_2(OCH_2C(CH_3)_3)_6$, illustrated in FIG. 3. These compounds have NMR (nuclear magnetic resonance) spectra, using the tetramethyl tin compound as reference, with a solution (THF-$d_5$) $^{119}Sn$ peaks at −128 ppm for $Sn_6O_4(OCH_2C(CH_3)_3)_4$ and at −251 and −257 ppm for $Sn_5O_2(OCH_2C(CH_3)_3)_6$. The solution state $^{119}Sn$ resonance for $[Sn(OCH_2C(CH_3)_3)_2]_n$ could not be obtained (presumably due to its low solubility); however, a $^{119}Sn$ solid state CP-MAS signal was observed at −214 ppm.

Table 1 shows the crystal data and structure refinement for polymeric $Sn(OCH_2C(CH_3)_3)_2$. The data reflects the polymeric nature of the compound in the empirical formula, where the data reflect a two-unit fragment. Table 2 shows the crystal data and structure refinement for $Sn_6O_4(OCH_2C(CH_3)_3)_4$. Table 3 shows the crystal data and structure refinement for $Sn_5O_2(OCH_2C(CH_3)_3)_6$. The temperature used was 168 K. The refinement method was a full-matrix least-squares on $F^2$. The data was corrected for absorption using the program SADABS.

TABLE 1

Crystal data and structure refinement for $Sn(OCH_2C(CH_3)_3)_2$.

| | |
|---|---|
| Empirical formula | $C_{20}H_{44}O_4Sn_2$ |
| Formula weight | 585.93 |
| Wavelength | 0.71073 A |
| Crystal system, space group | Triclinic, P1 |
| Unit cell dimensions | a = 6.1757(10) A alpha = 74.894(3) deg. |
| | b = 9.5349(15) A beta = 81.359(2) deg. |
| | c = 11.1180(17) A gamma = 85.962(3) deg. |
| Z, Calculated density | 1, 1.558 Mg/m$^3$ |
| Absorption coefficient | 2.019 mm$^{-1}$ |
| F(000) | 296 |
| Theta range for data colection | 1.92 to 23.30 deg. |
| Limiting indices | −6 <= h <= 6, −7 <= k <= 10, −11 <= I <= 12 |
| Reflections collected/unique | 2549/2088 [R(int) = 0.0132] |
| Data/restraints/parameters | 2088/3/147 |
| Goodness-of-fit on F$^2$ | 1.073 |
| Final R indices [I> 2sigma(I)] | R1 = 0.0306, wR2 = 0.0776 |
| R indices (all data) | R1 = 0.0321, wR2 = 0.0793 |

TABLE 2

Crystal data and structure refinement for $Sn_6O_4(OCH_2C(CH_3)_3)_4$.

| | |
|---|---|
| Empirical formula | $C_{40}H_{88}O_{16}Sn_{12}$ |
| Formula weight | 2249.38 |
| Wavelength | 0.71073 A |

TABLE 2-continued

Crystal data and structure refinement for $Sn_6O_4(OCH_2C(CH_3)_3)_4$.

| | |
|---|---|
| Crystal system, space group | Orthorhombic, P2(1)2(1)2(1) |
| Unit cell dimensions | a = 23.777(3) A alpha = 90 deg. |
| | b = 23.961(3) A beta = 90 deg. |
| | c = 11.9845(15) A gamma = 90 deg. |
| Z, Calculated density | 4, 2.188 Mg/m³ |
| Absorption coefficient | 4.356 mm⁻¹ |
| F(000) | 4224 |
| Theta range for data collection | 1.70 to 23.28 deg. |
| Limiting indices | −26 <= h <= 23, −26 <= k <= 25, −13 <= l <= 12 |
| Reflections collected/unique | 31180/9832 [R(int) = 0.0254] |
| Data/restraints/parameters | 9832/0/637 |
| Goodness-of-fit on F² | 1.019 |
| Final R indices [I> 2sigma(I)] | R1 = 0.0228, wR2 = 0.0549 |
| R indices (all data) | R1 = 0.0255, wR2 = 0.0561 |

TABLE 3

Crystal data and structure refinement for $Sn_5O_2(OCH_2C(CH_3)_3)_6$.

| | |
|---|---|
| Empirical formula | $C_{30}H_{66}O_8Sn_5$ |
| Formula weight | 1148.28 |
| Wavelength | 0.71073 A |
| Crystal system, space group | Triclinic, P-1 |
| Unit cell dimensions | a = 10.182(9) A alpha = 87.127(12) deg. |
| | b = 11.707(11) A beta = 84.157(13) deg. |
| | c = 20.167(18) A gamma = 64.555(11) deg. |
| Volume | 2159(3) A³ |
| Z, Calculated density | 2, 1.766 Mg/m³ |
| Absorption coefficient | 2.889 mm⁻¹ |
| F(000) | 1120 |
| Theta range for data collection | 2.03 to 23.36 deg. |
| Limiting indices | −11 <= h <= 10, −12 <= k <= 11, −20 <= l <= 22 |
| Reflections collected/unique | 9750/6100 [R(int) = 0.0321] |
| Data/restraints/parameters | 6100/0/406 |
| Goodness-of-fit on F² | 1.186 |
| Final R indices [I> 2sigma(I)] | R1 = 0.1120, wR2 = 0.2570 |
| R indices (all data) | R1 = 0.1354, wR2 = 0.2663 |

Tables 4, 5, and 6 provide the atomic coordinates (×10⁴) and equivalent isotropic displacement parameters (A²×10³) for polymeric $Sn(OCH_2C(CH_3)_3)_2$, $Sn_6O_4(OCH_2C(CH_3)_3)_4$, and $Sn_5O_2(OCH_2C(CH_3)_3)_6$, respectively. U(eq) os defined as one third of the trace of the orthogonalized $U_{ij}$ tensor.

TABLE 4

Atomic coordinates (× 10⁴) and equivalent isotropic displacement parameters (A² × 10³) for polymeric $Sn(OCH_2C(CH_3)_3)_2$.

| | x | y | z | U(eq) |
|---|---|---|---|---|
| C(1) | 6590(40) | 6990(20) | 10053(19) | 94(8) |
| C(2) | 5620(30) | 6194(16) | 11268(15) | 26(4) |
| C(3) | 5950(20) | 7531(13) | 11943(11) | 27(3) |
| C(4) | 3160(30) | 5910(20) | 11519(17) | 39(5) |
| C(5) | 6946(17) | 4894(12) | 11872(10) | 25(2) |
| C(6) | 8630(40) | 6600(20) | 7037(18) | 33(5) |
| C(7) | 9700(30) | 6111(17) | 5874(15) | 36(5) |
| C(8) | 12070(20) | 5630(17) | 5996(14) | 30(4) |
| C(9) | 8890(20) | 6924(15) | 4841(13) | 42(4) |
| C(10) | 8610(20) | 4732(15) | 5854(14) | 47(4) |
| C(11) | 11340(30) | 10650(20) | 8888(17) | 29(5) |

TABLE 4-continued

Atomic coordinates (× 10⁴) and equivalent isotropic displacement parameters (A² × 10³) for polymeric $Sn(OCH_2C(CH_3)_3)_2$.

| | x | y | z | U(eq) |
|---|---|---|---|---|
| C(12) | 10410(20) | 11252(15) | 10002(13) | 23(4) |
| C(13) | 11470(20) | 12731(14) | 9751(13) | 37(3) |
| C(14) | 10640(20) | 9904(15) | 11359(12) | 38(3) |
| C(15) | 7850(20) | 11328(17) | 10195(14) | 28(4) |
| C(16) | 3470(15) | 10504(11) | 6109(8) | 12(2) |
| C(17) | 4410(30) | 10784(17) | 4698(14) | 25(4) |
| C(18) | 4030(70) | 9620(40) | 4140(40) | 167(15) |
| C(19) | 3110(40) | 11910(20) | 3896(19) | 95(7) |
| C(20) | 6820(30) | 11048(18) | 4463(16) | 30(4) |
| O(1) | 5580(20) | 8042(16) | 9188(11) | 23(4) |
| O(2) | 4420(20) | 9094(15) | 6841(13) | 24(4) |
| O(3) | 9430(20) | 7937(16) | 7130(13) | 28(4) |
| O(4) | 10530(20) | 9284(15) | 8859(13) | 20(3) |
| Sn(1) | 7460(1) | 9554(1) | 7732(1) | 22(1) |
| Sn(2) | 2531(1) | 7580(1) | 8290(1) | 22(1) |

TABLE 5

Atomic coordinates (× 10⁴) and equivalent isotropic displacement parameters (A² × 10³) for $Sn_6O_4(OCH_2C(CH_3)_3)_4$.

| | x | y | z | U(eq) |
|---|---|---|---|---|
| Sn(1) | 5678(1) | 9507(1) | 7704(1) | 34(1) |
| Sn(2) | 6146(1) | 7540(1) | 6584(1) | 46(1) |
| Sn(3) | 6310(1) | 8336(1) | 9049(1) | 37(1) |
| Sn(4) | 6937(1) | 8834(1) | 6668(1) | 37(1) |
| Sn(5) | 4990(1) | 8257(1) | 7541(1) | 40(1) |
| Sn(6) | 5733(1) | 8773(1) | 5113(1) | 40(1) |
| Sn(7) | 8158(1) | 8922(1) | 3997(1) | 37(1) |
| Sn(8) | 8631(1) | 8175(1) | 1698(1) | 40(1) |
| Sn(9) | 7421(1) | 9083(1) | 1480(1) | 43(1) |
| Sn(10) | 8246(1) | 10187(1) | 2373(1) | 41(1) |
| Sn(11) | 9418(1) | 9353(1) | 2672(1) | 40(1) |
| Sn(12) | 8707(1) | 9344(1) | 53(1) | 39(1) |
| O(1) | 6381(2) | 9017(2) | 7977(3) | 34(1) |
| O(2) | 5339(2) | 8920(2) | 6622(3) | 32(1) |
| O(3) | 6361(2) | 8300(2) | 5877(3) | 39(1) |
| O(4) | 5775(2) | 7927(2) | 7953(4) | 39(1) |
| O(5) | 5300(2) | 8908(2) | 8884(3) | 35(1) |
| O(6) | 5303(2) | 7761(2) | 5988(4) | 56(1) |
| O(7) | 6960(2) | 8051(2) | 7879(4) | 49(1) |
| O(8) | 6304(2) | 9423(2) | 5736(4) | 43(1) |
| O(9) | 8841(2) | 8723(2) | 2975(3) | 35(1) |
| O(10) | 8167(2) | 8784(2) | 829(3) | 39(1) |
| O(11) | 7819(2) | 9461(2) | 2835(4) | 36(1) |
| O(12) | 8881(2) | 9745(2) | 1551(4) | 37(1) |
| O(13) | 7782(2) | 8302(2) | 2830(4) | 44(1) |
| O(14) | 9311(2) | 8728(2) | 812(4) | 52(1) |
| O(15) | 7748(2) | 9885(2) | 719(5) | 63(2) |
| O(16) | 8841(2) | 9807(2) | 3811(4) | 49(1) |
| C(1) | 4877(3) | 9101(3) | 9631(6) | 44(2) |
| C(2) | 4919(3) | 8865(3) | 10795(6) | 46(2) |
| C(3) | 4385(4) | 9078(4) | 11437(7) | 73(3) |
| C(4) | 4884(4) | 8231(3) | 10745(7) | 78(3) |
| C(5) | 5436(4) | 9061(5) | 11372(8) | 88(3) |
| C(6) | 4946(4) | 7287(4) | 5656(7) | 71(3) |
| C(7) | 4695(4) | 7349(3) | 4539(6) | 46(2) |
| C(8) | 4322(4) | 7864(4) | 4477(11) | 105(4) |
| C(9) | 5177(4) | 7377(4) | 3682(8) | 85(3) |
| C(10) | 4363(4) | 6825(4) | 4275(8) | 86(3) |
| C(11) | 7523(4) | 7950(4) | 8329(7) | 65(2) |
| C(12) | 7778(4) | 7424(3) | 7909(6) | 48(2) |
| C(13) | 7813(4) | 7428(4) | 6628(7) | 69(3) |
| C(14) | 8370(4) | 7364(5) | 8409(9) | 101(4) |
| C(15) | 7440(5) | 6926(4) | 8278(9) | 99(4) |
| C(16) | 6576(4) | 9750(3) | 4875(7) | 57(2) |
| C(17) | 6346(3) | 10341(3) | 4769(6) | 47(2) |
| C(18) | 6650(3) | 10621(4) | 3802(7) | 66(2) |
| C(19) | 5720(3) | 10327(3) | 4566(8) | 61(2) |
| C(20) | 6478(4) | 10665(4) | 5817(8) | 72(3) |

TABLE 5-continued

Atomic coordinates (× 10$^4$) and equivalent isotropic displacement parameters (A$^2$ × 10$^3$) for Sn$_6$O$_4$(OCH$_2$C(CH$_3$)$_3$)$_4$.

| | x | y | z | U(eq) |
|---|---|---|---|---|
| C(21) | 7561(6) | 7816(5) | 3332(7) | 133(6) |
| C(22) | 7154(3) | 7487(3) | 2809(6) | 49(2) |
| C(23) | 6607(5) | 7879(5) | 2848(10) | 111(4) |
| C(24) | 6962(5) | 6986(4) | 3379(8) | 113(5) |
| C(25) | 7247(3) | 7390(3) | 1570(6) | 49(2) |
| C(26) | 9678(3) | 8443(3) | 35(8) | 62(2) |
| C(27) | 10263(3) | 8639(3) | −10(6) | 41(2) |
| C(28) | 10587(4) | 8321(3) | −897(8) | 74(3) |
| C(29) | 10303(4) | 9255(3) | −218(8) | 66(2) |
| C(30) | 10545(4) | 8516(4) | 1103(7) | 81(3) |
| C(31) | 7299(4) | 10303(4) | 443(7) | 66(2) |
| C(32) | 7402(3) | 10495(3) | −701(6) | 43(2) |
| C(33) | 7410(4) | 10007(4) | −1552(8) | 85(3) |
| C(34) | 7963(3) | 10810(3) | −770(7) | 58(2) |
| C(35) | 6926(4) | 10898(4) | −1039(9) | 80(3) |
| C(36) | 9088(4) | 10242(5) | 4497(9) | 103(4) |
| C(37) | 8855(3) | 10310(3) | 5605(6) | 49(2) |
| C(38) | 9158(4) | 10741(5) | 6263(12) | 15(6) |
| C(39) | 8964(6) | 9767(5) | 6281(10) | 119(4) |
| C(40) | 8237(3) | 10403(4) | 5595(7) | 67(3) |

TABLE 6

Atomic coordinates (× 10$^4$) and equivalent isotropic displacement parameters (A$^2$ × 10$^3$) for Sn$_5$(O)$_2$(ONep)$_6$.

| | x | y | z | U(eq) |
|---|---|---|---|---|
| Sn(1) | 7001(2) | 5723(2) | 1270(1) | 37(1) |
| Sn(2) | 9572(2) | 5744(2) | 2249(1) | 46(1) |
| Sn(3) | 7283(2) | 5745(2) | 3763(1) | 38(1) |
| Sn(4) | 4707(2) | 5647(2) | 2812(1) | 46(1) |
| Sn(5) | 8313(2) | 3340(2) | 2523(1) | 44(1) |
| O(1) | 8521(19) | 4716(18) | 1913(10) | 45(5) |
| O(2) | 6760(20) | 4687(16) | 3141(11) | 50(5) |
| O(3) | 8076(18) | 6913(16) | 1467(8) | 36(4) |
| O(4) | 7850(20) | 6855(19) | 3011(9) | 45(5) |
| O(5) | 9580(30) | 4410(30) | 3138(15) | 100(10) |
| O(6) | 4966(18) | 6890(17) | 3556(8) | 39(4) |
| O(7) | 5290(18) | 6703(18) | 2034(8) | 40(5) |
| O(8) | 6230(30) | 4140(20) | 1988(12) | 76(8) |
| C(1) | 8280(30) | 7900(20) | 1131(12) | 34(6) |
| C(2) | 9120(30) | 7650(20) | 448(11) | 34(6) |
| C(3) | 10530(50) | 6480(30) | 490(17) | 94(16) |
| C(4) | 9350(40) | 8780(30) | 207(14) | 55(8) |
| C(5) | 8310(60) | 7290(50) | −60(20) | 130(20) |
| C(6) | 7170(40) | 8190(30) | 2981(14) | 49(8) |
| C(7) | 7810(40) | 8850(30) | 3378(13) | 58(10) |
| C(8) | 9370(60) | 8540(60) | 3080(20) | 150(30) |
| C(9) | 6940(60) | 10300(40) | 3280(20) | 107(17) |
| C(10) | 7780(70) | 8470(50) | 4109(17) | 130(20) |
| C(11) | 10740(70) | 4300(60) | 3650(20) | 150(20) |
| C(12) | 11680(30) | 2910(30) | 3714(15) | 50(8) |
| C(13) | 12980(50) | 2710(100) | 4010(30) | 310(70) |
| C(14) | 10760(60) | 2330(60) | 4070(30) | 140(20) |
| C(15) | 11970(120) | 2560(100) | 3000(20) | 320(70) |
| C(16) | 3750(30) | 7900(30) | 3883(12) | 36(6) |
| C(17) | 3170(30) | 7560(30) | 4544(12) | 45(8) |
| C(18) | 4200(40) | 7200(50) | 5089(14) | 100(16) |
| C(19) | 1800(30) | 8750(30) | 4773(16) | 60(9) |
| C(20) | 2670(50) | 6520(30) | 4460(20) | 109(18) |
| C(21) | 4610(30) | 8040(30) | 2037(12) | 36(6) |
| C(22) | 3270(30) | 8680(30) | 1645(13) | 51(9) |
| C(23) | 2680(50) | 10030(40) | 1730(20) | 120(20) |
| C(24) | 3750(40) | 8420(40) | 892(16) | 106(18) |
| C(25) | 2150(40) | 8190(60) | 1890(30) | 170(30) |
| C(26) | 5660(60) | 3110(50) | 1900(30) | 140(20) |
| C(27) | 5440(40) | 2930(30) | 1239(18) | 61(9) |
| C(28) | 7000(50) | 2410(50) | 850(20) | 114(19) |

TABLE 6-continued

Atomic coordinates (× 10$^4$) and equivalent isotropic displacement parameters (A$^2$ × 10$^3$) for Sn$_5$(O)$_2$(ONep)$_6$.

| | x | y | z | U(eq) |
|---|---|---|---|---|
| C(29) | 4550(60) | 4170(50) | 950(30) | 160(30) |
| C(30) | 4900(70) | 2070(60) | 1190(30) | 200(40) |

In the method of the present invention, the addition of water to polymeric Sn(OCH$_2$C(CH$_3$)$_3$)$_2$ in a non-reactive solvent yields the products Sn$_6$O$_4$(OCH$_2$C(CH$_3$)$_3$)$_4$ and Sn$_5$O$_2$(OCH$_2$C(CH$_3$)$_3$)$_6$. The amount of water added can vary between one-tenth (0.1) and two (2) moles of water per mole of polymeric Sn(OCH$_2$C(CH$_3$)$_3$)$_2$. Advantageously, the selectivity of the hydrolysis products can be controlled by the amount of water added. When greater than approximately one-third moles and less than two moles of water are added per mole of polymeric Sn(OCH$_2$C(CH$_3$)$_3$)$_2$, Sn$_6$O$_4$(OCH$_2$C(CH$_3$)$_3$)$_4$ is produced. When approximately two-thirds moles of water (and more generally, 0.5 to 0.75 moles water) are added per mole of polymeric Sn(OCH$_2$C(CH$_3$)$_3$)$_2$, Sn$_6$O$_4$(OCH$_2$C(CH$_3$)$_3$)$_4$ is preferentially produced. When between approximately one-fourth and two-thirds moles of water are added per mole of polymeric Sn(OCH$_2$C(CH$_3$)$_3$)$_2$, Sn$_5$O$_2$(OCH$_2$C(CH$_3$)$_3$)$_6$ is produced. When approximately two-fifths moles of water (and more generally, 0.3 to 0.5 moles water) are added per mole of polymeric Sn(OCH$_2$C(CH$_3$)$_3$)$_2$, Sn$_5$O$_2$(OCH$_2$C(CH$_3$)$_3$)$_6$ is preferentially produced. The reactions proceed at room temperature.

Metals other than tin in these compounds were investigated but do not produce structures with accessible electrons similar to the tin alkoxides. This is considered to be partially the result of the size and charge of the tin atoms. The large size to small cation ratio allows for the arrangement to be observed. For other systems, the cation have too great a charge or the charge is variable, or the size of the cation is inappropriate. Furthermore, the alkoxide group OCH$_2$C(CH$_3$)$_3$ is unique, in comparison to standard alkoxy groups, to introduce substantial steric bulk without completely shutting down the reactivity at the metal center. For example the OCH(CH$_3$)$_2$ group does not possess enough steric bulk to limit oligomerization; however, the OC(CH$_3$)$_3$ group completely shuts down the metal centers.

In one embodiment, the polymeric tin alkoxide, Sn(OCH$_2$C(CH$_3$)$_3$)$_2$, is formulated by dissolving a precursor tin compound, such as (Sn(N(CH$_3$)$_2$)$_2$)$_2$ in a non-reactive solvent (that is, a solvent which does not react with the precursor tin compound or subsequent tin alkoxide compounds), where the solvent can be any polar or non-polar organic solvent in which the precursor compound is soluble. Such solvents include, but are not limited to alkanes, alkyl organic solvents, aryl organic solvents, and polar solvents. Examples of these solvents would include hexanes, toluene, tetrahydrofuran (THF), and pyridine. Alcohols and ketones should not be used as these solvents react with metal alkoxides. In one embodiment, HOCH$_2$C(CH$_3$)$_3$ is added and the solution mixed, such as by stirring. The volatile material of the reaction can be removed in vacuo to produce a white powder which was identified as [Sn(OCH$_2$C(CH$_3$)$_3$)$_2$]$_n$.

Figure 2:
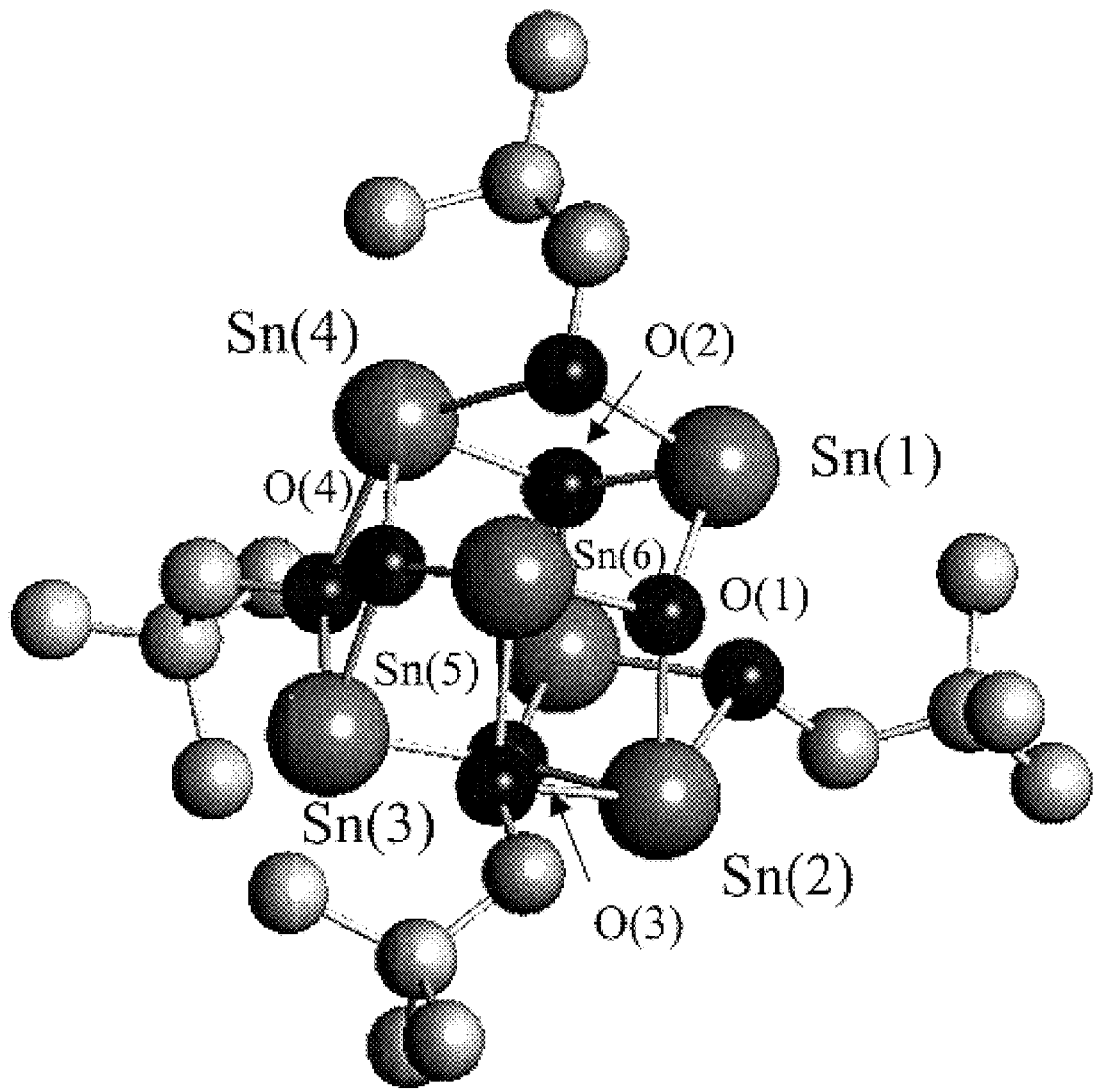
FIG. 2 illustrates the structure of $Sn_6O_4(OCH_2C(CH_3)_3)_4$.
Figure 3:
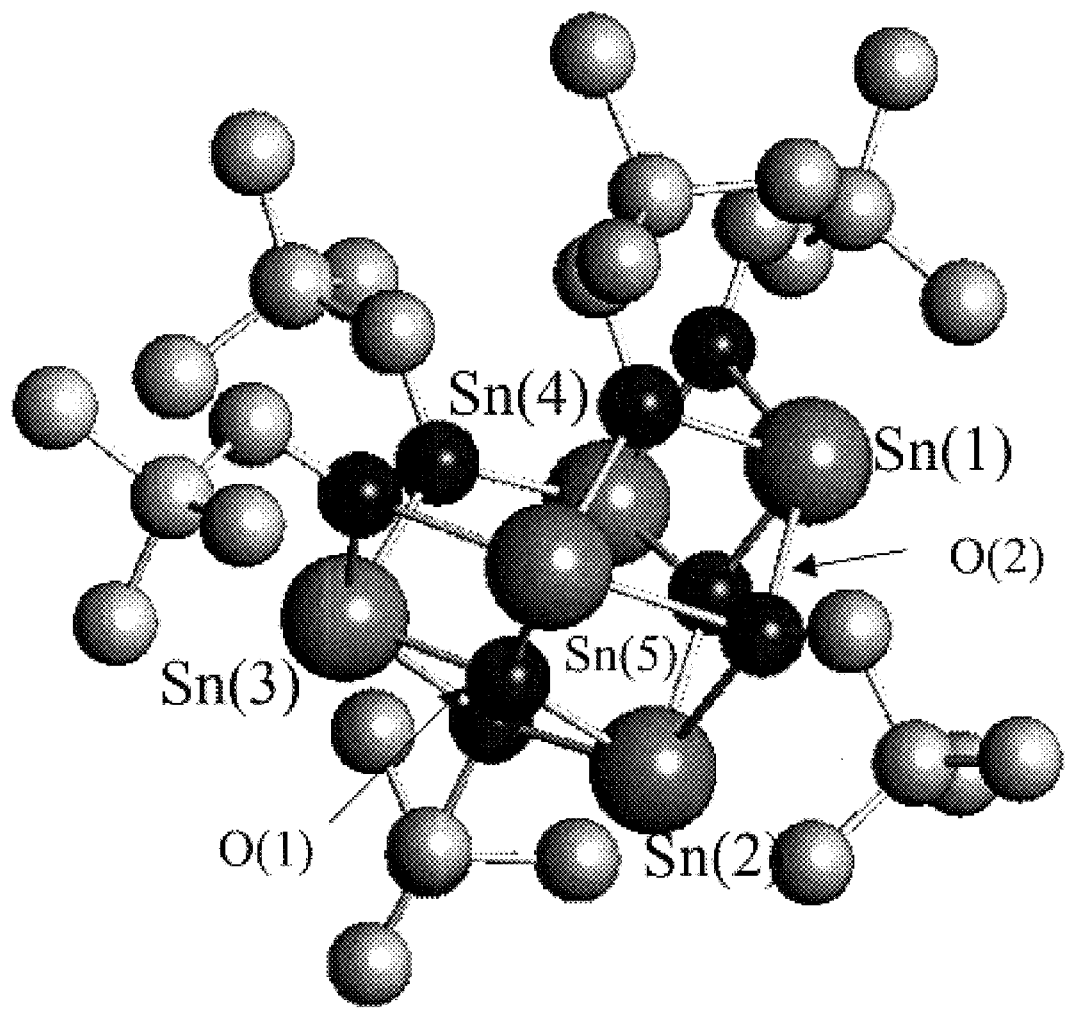
FIG. 3 illustrates the structure of $Sn_5O_2(OCH_2C(CH_3)_3)_6$.

In one embodiment to make one hydrolysis product of the polymeric tin alkoxide, [Sn(OCH$_2$C(CH$_3$)$_3$)$_2$]$_n$, the polymeric tin alkoxide [Sn(OCH$_2$C(CH$_3$)$_3$)$_2$]$_n$, is first dissolved in a suitable non-reactive polar or non-polar organic solvent. Approximately two-thirds of a mole of water is added and the solution, stirred, warmed, concentrated, and allowed to set to produce crystals of $Sn_6O_4(OCH_2C(CH_3)_3)_4$. As seen in FIG. 2, this hydrolysis product contains both $\mu_2$ and $\mu_3$ bonding (i.e., some of the tin atoms are bonded to two other atoms and some are bonded to three other atoms), in contrast to the product of the same chemical formula described by Sita et al. (1997) which contains only $\mu_3$ bonding. This results in an NMR spectra with a tin peak at −128 ppm using a tetramethyl tin compound as reference.

When adding the water to the solution, care must be taken to add water slowly. The slow addition insures a uniform, homogeneous reaction occurs instead of concentrated hydrolysis around any droplets that would be added by fast addition. Water can also be added such means as by slow evaporation of a droplet into a stirring mixture. In this method the water droplet is place onto the side of a flask which does not fall into the solution. After several hours, the water droplet will evaporate and the solution will be clear. Another method is to pre-dissolve the water in the parent solvent to fully disperse it. This is then slowly added to the Sn precursors and allowed to react. The same products were isolated in either route.

In another embodiment to make $Sn_6O_4(OCH_2C(CH_3)_3)_4$, the polymeric tin alkoxide $[Sn(OCH_2C(CH_3)_3)_2]_n$ is first dissolved in a suitable non-reactive polar or non-polar organic solvent and reacted with a carboxylic acid, such as acetic acid, iso-butyric acid, trimethyl acetic acid, and t-butyl acetic acid. The solution is stirred, warmed, concentrated, and allowed to set to produce crystals of $Sn_6O_4(OCH_2C(CH_3)_3)_4$.

In an embodiment to make the other hydrolysis product, $Sn_5O_2(OCH_2C(CH_3)_3)_6$, of the polymeric tin alkoxide, $[Sn(OCH_2C(CH_3)_3)_2]_n$, the polymeric tin alkoxide $[Sn(OCH_2C(CH_3)_3)_2]_n$ is first dissolved in a suitable non-reactive polar or non-polar organic solvent. Approximately two-fifths of a mole equivalent of water is added and the solution allowed to set to produce crystals of $Sn_5O_2(OCH_2C(CH_3)_3)_6$.

Once the crystals were formed, typically by slow evaporation, single crystal X-ray diffraction experiments were undertaken to determine structure and other characteristics. All crystals were mounted onto a thin glass fiber and immediately placed under a liquid $N_2$ stream, on a Bruker AXS diffractometer. The radiation used was graphite monochromatized Mo K$\alpha$ radiation ($\lambda$=0.71073 A). The lattice parameters were optimized from a least-squares calculation on 58 carefully centered reflections. Lattice determination, data collection, data reduction, structure solution, and structure refinement was performed and the data corrected for absorption.

Each structure was solved using direct methods that yielded the heavier atoms, along with a number of the C atoms. Subsequent Fourier synthesis yielded the remaining C atom positions. The hydrogen atoms were fixed in positions of ideal geometry and refined. These idealized hydrogen atoms had their isotropic temperature factors fixed at 1.2 or 1.5 times the equivalent isotropic U of the C atoms they were bonded to. The final refinement of each compound included anisotropic thermal parameters on all non-hydrogen atoms.

EXAMPLES

All compounds were synthesized under inert atmosphere conditions using standard glove-box techniques. All solvents were dried over Na°/benzophenone and stored over sieves immediately prior to use. $HOCH_2C(CH_3)_3$ was used as received from Aldrich. Distilled and de-ionized $H_2O$ was used for hydrolysis reactions. $[Sn(NMe_2)_2]_2$ was prepared according to standard methods.

Example 1

Preparation of $[Sn(OCH_2C(CH_3)_3)_2]_n$

In a vial, $[Sn(N(CH_3)_2)_2]_2$ was dissolved in hexanes. Two equivalents of $HOCH_2C(CH_3)_3$ were added and the reaction was stirred overnight. After warming slightly for 1 hour, the volatile material of the reaction was removed in vacuo. The final product was washed with hexanes to remove any residual starting materials. X-ray quality crystals were isolated from hot tetrahydrofuran (THF).

Example 2

Preparation of $Sn_6(O)_4(OCH_2C(CH_3)_3)_4$

In a flask, $[Sn(OCH_2C(CH_3)_3)_2]_n$ was dissolved in THF. Two-thirds of an equivalent of $H_2O$ was added to the side of the flask and allowed to slowly dissipate into the solution mixture. The water was not directly added to the solution. The volume of the reaction mixture was drastically reduced and allowed to set at room temperature yielding crystals of $Sn_6(O)_4(OCH_2C(CH_3)_3)_4$.

Example 3

Preparation of $Sn_5(O)_2(OCH_2C(CH_3)_3)_6$

In a flask, $[Sn(OCH_2C(CH_3)_3)_2]_n$ was dissolved in THF. Two-fifths of an equivalent of $H_2O$ was added to the side of the flask and allowed to slowly dissipate into the solution mixture. The water was not directly added to the solution. The volume of the reaction mixture was drastically reduced and allowed to set at room temperature yielding crystals $Sn_5(O)_2(OCH_2C(CH_3)_3)_6$.

Example 4

Preparation of $Sn_6(O)_4(OCH_2C(CH_3)_3)_4$ Using Carboxylic Acids

In a flask, $[Sn(OCH_2C(CH_3)_3)_2]_n$ was dissolved in toluene. Acetic acid was added via pipette and the reaction was stirred for 12 hours. After this time, the reaction was warmed for 1 hour and then allowed to set until crystal formed. These proved to be $Sn_6(O)_4(OCH_2C(CH_3)_3)_4$.

The invention being thus described, it will be apparent to those skilled in the art that the same may be varied in many ways. Such variations are not to be regarded as a departure from the spirit and scope of the invention, and all such modifications are intended to be included within the scope of the following claims.

We claim:
1. The polymer $Sn(OCH_2C(CH_3)_3)_2$.
2. The hydrolysis compound $Sn_5(O)_2(OCH_2C(CH_3)_3)_6$.
3. The hydrolysis compound $Sn_5(O)_2(OCH_2C(CH_3)_3)_6$ of claim 2 produced by dissolving the polymer $Sn(OCH_2C(CH_3)_3)_2$ in a solvent to form a solution and reacting said solution with water.
4. The hydrolysis compound $Sn_5(O)_2(OCH_2C(CH_3)_3)_6$ of claim 3 wherein said water is added at a ration between 0.1 moles to 2 moles water per mole of the polymer $Sn(OCH_2C(CH_3)_3)_2$.
5. The hydrolysis compound $Sn_5(O)_2(OCH_2C(CH_3)_3)_6$ of claim 4 wherein said water is added at a ration between 0.3 moles to 0.5 moles water per mole of the polymer $Sn(OCH_2C(CH_3)_3)_2$.
6. The hydrolysis compound $Sn_5(O)_2(OCH_2C(CH_3)_3)_6$ of claim 2 wherein the hydrolysis compound $Sn_5(O)_2(OCH_2C(CH_3)_3)_6$ has nuclear magnetic resonance spectrum $^{119}Sn$ peaks at approximately −251 and −257 ppm.
7. The hydrolysis compound $Sn_5(O)_2(OCH_2C(CH_3)_3)_6$ of claim 3 wherein said solvent is a non-reactive organic solvent selected from alkanes, alkyl organic solvents, aryl organic solvents and polar solvents.

8. The hydrolysis compound $Sn_5(O)_2(OCH_2C(CH_3)_3)_6$ of claim 3 wherein said solvent is selected from hexane, toluene, pyridine compounds, and tetrahydrofuran.

9. The hydrolysis compound $Sn_6(O)_4(OCH_2C(CH_3)_3)_4$.

10. The hydrolysis compound $Sn_6(O)_4(OCH_2C(CH_3)_3)_4$ of claim 9 produced by dissolving the polymer $Sn(OCH_2C(CH_3)_3)_2$ in a solvent to form a solution and reacting said solution with water.

11. The hydrolysis compound $Sn_6(O)_4(OCH_2C(CH_3)_3)_4$ of claim 10 wherein said water is added at a ration between 0.1 moles to 2 moles water per mole of the polymer $Sn(OCH_2C(CH_3)_3)_2$.

12. The hydrolysis compound $Sn_6(O)_4(OCH_2C(CH_3)_3)_4$ of claim 11 wherein said water is added at a ration between 0.5 moles to 0.75 moles water per mole of the polymer $Sn(OCH_2C(CH_3)_3)_2$.

13. The hydrolysis compound $Sn_6(O)_4(OCH_2C(CH_3)_3)_4$ of claim 9 wherein the hydrolysis compound $Sn_6(O)_4(OCH_2C(CH_3)_3)_4$ has a nuclear magnetic resonance spectrum $^{119}Sn$ peak at approximately −128 ppm.

14. The hydrolysis compound $Sn_6(O)_4(OCH_2C(CH_3)_3)_4$ of claim 10 wherein said solvent is a non-reactive organic solvent selected from alkanes, alkyl organic solvents, aryl organic solvents and polar solvents.

15. The hydrolysis compound $Sn_6(O)_4(OCH_2C(CH_3)_3)_4$ of claim 10 wherein said solvent is selected from hexane, toluene, pyridine compounds, and tetrahydrofuran.

16. The hydrolysis compound $Sn_6(O)_4(OCH_2C(CH_3)_3)_4$ of claim 9 produced by dissolving the polymer $Sn(OCH_2C(CH_3)_3)_2$ in a solvent to form a solution and reacting said solution with a carboxylic acid.

17. A method of making $Sn(OCH_2C(CH_3)_3)_2$ comprising dissolving $Sn(N(CH_3)_2)_2)_2$ in a solvent and reacting with $HOCH_2C(CH_3)_3$.

18. A method of making the hydrolysis products $Sn_6(O)_4(OCH_2C(CH_3)_3)_4$ and $Sn_5(O)_2(OCH_2C(CH_3)_3)_6$ comprising dissolving $Sn(OCH_2C(CH_3)_3)_2$ in a non-reative organic solvent to form a solution and adding water to said solution.

19. The method of claim 18 wherein adding water to said solution is performed by evaporation into said solution.

20. A method of making the hydrolysis products $Sn_6(O)_4(OCH_2C(CH_3)_3)_4$ and $Sn_5(O)_2(OCH_2C(CH_3)_3)_6$ comprising pre-dissolving water into a non-reactive organic solvent and reacting with $Sn(OCH_2C(CH_3)_3)_2$.

* * * * *